(12) United States Patent
Iversen

(10) Patent No.: US 6,764,680 B2
(45) Date of Patent: Jul. 20, 2004

(54) COMBINED APPROACH TO TREATMENT OF CANCER WITH HCG VACCINES

(75) Inventor: Patrick L. Iversen, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 0 days.

(21) Appl. No.: 09/915,676

(22) Filed: Jul. 26, 2001

(65) Prior Publication Data

US 2002/0164338 A1 Nov. 7, 2002

Related U.S. Application Data

(62) Division of application No. 09/571,497, filed on May 15, 2000, now abandoned.
(60) Provisional application No. 60/134,419, filed on May 17, 1999, and provisional application No. 60/134,432, filed on May 17, 1999.

(51) Int. Cl.⁷ ............................................. A61K 39/345
(52) U.S. Cl. ................................ 424/130.1; 424/133.1; 424/142.1; 424/155.1; 424/185.1; 530/387.1; 530/300
(58) Field of Search ........................... 424/130.1, 133.1, 424/142.1, 155.1, 185.1; 530/387.1, 300

(56) References Cited

U.S. PATENT DOCUMENTS

| | | |
|---|---|---|
| 4,691,006 A | 9/1987 | Stevens |
| 6,319,504 B1 * | 11/2001 | Gallo et al. .............. 424/198.1 |

OTHER PUBLICATIONS

Acevedo, H F et al, 1987, Cancer Detect Prev, 1 (Suppl): 477–486.*
Berger, P., et al., "Immunochemical mapping of gonadtropins," *Molecular and Cellular Endocrinologyl*, 125: 33–43 (1996).
Bodey, B., et al., "Failure of cancer vaccines: the significant limitations of this approach to immunotherapy," *Anticancer Research*, 20: 2665–2676 (2000).
Chang, S.P., et al., "Immunologic memory to phophorylchonine, II. PC–KLH induces two antibody populations that dominate different isotypes," *Journal of Immunology*, 128: 702–705 (1982).
Creemers, P., et al., "Effect of a mouse mammary tumor virus–derived protein vaccine on primary tumor development in mice," *Journal of the National Cancer Institute*, 60: 1461–1466 (1978).
Dirnhofer, S., et al., "The molecular basis for epitopes on the free β–subunit of human chorionic gonadotrophin (hCG), its carboxyl–terminal peptide and the hCGβ–core fragment" *Journal of Endocrinology* 141:153–162 (1994).

Ezzell, C., "Cancer 'vaccines': an idea whose name has come?", *Journal of the National Cancer Institute*, 7: 46–49 (1995).
Rock, E.P., et al., "Immunogenicity of a fusion protein linking the beta subunit carboxyl terminal peptide (CTP) of human chorionic gonadotropin to the B subunit of *Escherichia coli* heat–labile enterotoxin (LTB)," *Vaccine*, 14 1560–1568 (1996).
Rose, N.R., et al., "Immunologic hazards associated with vaccinations of humans," *Journal of Autoimmunity*, 14 11–13 (2000).
Spitler, L.E., "Cancer vaccines : the interferon analogy," *Cancer Biotherapy*, 10: 1–3 (1995).
* Talwar, G.P., "Vaccines for control of fertility and hormone–dependent cancers," *Immunology and Cell Biology*, 75:2 184–189 (1997).
Triozzi, P.L., et al., "Effects of a β–Human Chorionic Gonadotropin Subunit Immunogen Administered in Aqueous Solution with a Novel Nonionic Block Copolymer Adjuvant in Patients with Advanced Cancer" *Clinical Cancer Research* 3:2355–2362 (1997).
Triozzi, P.L., et al, "Human chorionic gonadotropin as a target for cancer vaccines (Review) " *Oncology Reports* 6:7–17 (1999).
Triozzi, P.L., et al., "Phase Ib Trial of a Synthetic β Human Chorionic Gonadotropin Vaccine in Patients with Metastatic Cancer" *Specific Immunotherapy of Cancer with Vaccines* Bystryn, et al., (Eds.) Annals of the New York Academy of Sciences vol. 690, New York (1993).
Vitetta, E.S., et al., "Monoclonal antibodies as agonists: an expanded role for their use in cancer therapy," *Cancer Research*, 54: 5301–5309 (1994).
Yakeishi, Y., et al., "Distribution of beta–human chorionic gonadotropin–positive cells in noncancerous gastric mucosa and in malignant gastric tumors," 66: 695–701 (1990).
Snyder, L.L., et al., "Synthetic Hormone/Growth Factor Subunit Vaccine with Application to Antifertility and Cancer" *Vaccine Design: The Subunit and Adjuvant Approach* Powell et al. (Eds.) Plenum Press, New York (1995), pp. 907–930.

* cited by examiner

*Primary Examiner*—Susan Ungar
*Assistant Examiner*—Minh-Tam Davis
(74) *Attorney, Agent, or Firm*—Perkins Coie LLP

(57) ABSTRACT

The invention relates to an improved method for immunotherapy of cancer by administering to a subject a human anti-hCG monoclonal antibody and/or an hCG immunogenic peptide vaccine, followed by monitoring the patient's immune response to hCG-CTP16, hCG-CTP21 and hCG-CTP37, respectively, and adjusting the vaccination regimen according to the detectable immune response to the hCG immunogenic peptides. The invention further relates to devices, methods and kits for immunoassay of hCG immunogenic peptides.

1 Claim, 4 Drawing Sheets

1   MEMFQGLLLL LLLSMGGTWA SKEPLRPRCR PINATLAVEK EGCPVCITVN TTICAGYCPT
61  MTRVLQGVLP ALPQVVCNYR DVRFESIRLP GCPRGVNPVV SYAVALSCQC ALCRRSTTDC
121 GGPKDHPLTC DDPRFQDSSS SKAPPPSLPS PSRLPGPSDT PILPQ

Fig. 1

TCDDPRFQDSSSSKAPPPSLPSPSRLPGPSDTPILPQ

Fig. 2A

MTCDDPRFQDSSSSKAPPPSLPSPSRLPGPSDTPILPQ

Fig. 2B

CDDPRFQDSSSSKAPPPSLPS

Fig. 2C

DDPRFQDS

Fig. 2D

SPSRLPGPSDTPILPQ

Fig. 2E

CSPSRLPGPSDTPILPQ

Fig. 2F

RLPGPSDTPILPQ

Fig. 2G

CPTMTRVLQGVLPALPQVVC

Fig. 2H

SEQUENCE LISTING

<160> NUMBER OF SEQ ID NOS: 9

<210> SEQ ID NO 1
<211> LENGTH: 165
<212> TYPE: PRT
<213> ORGANISM: Homo sapiens

<400> SEQUENCE: 1

```
Met Glu Met Phe Gln Gly Leu Leu Leu Leu Leu Leu Ser Met Gly
 1               5                  10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
```

165

<210> SEQ ID NO 2
<211> LENGTH: 37
<212> TYPE: PRT
<213> ORGANISM: Homo sapiens

<400> SEQUENCE: 2

Thr Cys Asp Asp Pro Arg Phe Gln Asp Ser Ser Ser Ser Lys Ala Pro
1               5                   10                  15

Pro Pro Ser Leu Pro Ser Pro Ser Arg Leu Pro Gly Pro Ser Asp Thr
            20                  25                  30

Pro Ile Leu Pro Gln
        35

<210> SEQ ID NO 3
<211> LENGTH: 38
<212> TYPE: PRT
<213> ORGANISM: Artificial Sequence
<220> FEATURE:
<223> OTHER INFORMATION: C-terminal peptide of hCG with N-terminal
      methionine

<400> SEQUENCE: 3

Met Thr Cys Asp Asp Pro Arg Phe Gln Asp Ser Ser Ser Ser Lys Ala
1               5                   10                  15

Pro Pro Pro Ser Leu Pro Ser Pro Ser Arg Leu Pro Gly Pro Ser Asp
            20                  25                  30

Thr Pro Ile Leu Pro Gln
        35

<210> SEQ ID NO 4
<211> LENGTH: 21
<212> TYPE: PRT
<213> ORGANISM: Homo sapiens

<400> SEQUENCE: 4

Cys Asp Asp Pro Arg Phe Gln Asp Ser Ser Ser Ser Lys Ala Pro Pro
1               5                   10                  15

Pro Ser Leu Pro Ser
            20

<210> SEQ ID NO 5
<211> LENGTH: 8
<212> TYPE: PRT
<213> ORGANISM: Homo sapiens

<400> SEQUENCE: 5

Asp Asp Pro Arg Phe Gln Asp Ser
1               5

<210> SEQ ID NO 6
<211> LENGTH: 16
<212> TYPE: PRT
<213> ORGANISM: Homo sapiens

<400> SEQUENCE: 6

Ser Pro Ser Arg Leu Pro Gly Pro Ser Asp Thr Pro Ile Leu Pro Gln
1               5                   10                  15

<210> SEQ ID NO 7
<211> LENGTH: 17
<212> TYPE: PRT

-continued

```
<213> ORGANISM: Artificial Sequence
<220> FEATURE:
<223> OTHER INFORMATION: residues 150-165 of beta subunit of hCG with
      added N-terminal C

<400> SEQUENCE: 7

Cys Ser Pro Ser Arg Leu Pro Gly Pro Ser Asp Thr Pro Ile Leu Pro Gln
1               5                   10                  15

<210> SEQ ID NO 8
<211> LENGTH: 13
<212> TYPE: PRT
<213> ORGANISM: Homo sapiens

<400> SEQUENCE: 8

Arg Leu Pro Gly Pro Ser Asp Thr Pro Ile Leu Pro Gln
1               5                   10

<210> SEQ ID NO 9
<211> LENGTH: 20
<212> TYPE: PRT
<213> ORGANISM: Homo sapiens

<400> SEQUENCE: 9

Cys Pro Thr Met Thr Arg Val Leu Gln Gly Val Leu Pro Ala Leu Pro
1               5                   10                  15

Gln Val Val Cys
            20
```

COMBINED APPROACH TO TREATMENT OF CANCER WITH HCG VACCINES

This application is a division of application Ser. No. 09/571,497, filed May 15, 2000, now abandoned, which claims priority to U.S. provisional applications having Serial Nos. 60/134,419 and 60/134,432, both filed on May 17, 1999, all of which are hereby incorporated by reference in their entirety.

FIELD OF THE INVENTION

The invention is concerned with methods for in vivo immunotherapy of cancers associated with production of human chorionic gonadotropin (hCG) by administering a human anti-hCG monoclonal antibody and/or an hCG immunogenic peptide vaccine. The invention further relates to methods and devices for monitoring and adjusting the treatment regimen of patients, based on the results of an evaluation of the immune response to the 37 mer C-terminal fragment of hCG (hCG-CTP37) and immunogenic fragments thereof.

References

Abbas, A K, et al., Eds., *Cellular and Molecular Immunology*, 3$^{rd}$ edition. W B Saunders Co., 394–405 (1997)

Acevedo, et al., *Cancer* 69:1829–1842 (1992)

Acevedo, et al, *Cancer Detect. Prev.* 1(Suppl.):447–287 (1987)

Braunstein, G D, In: IMMUNODAIGNOSIS OF CANCER, Herberman, R B and Mercer, D W, Eds, Marcel Dekker, Inc., New York, pages 673–701 (1990)

Dirnhofer, et al., *Hum Pathol April;* 29(4):377–82 (1998)

Fiddes, J. C. and Goodman, H. M. Nature, 281: 351–356 (1979)

Fiddes, J. C. and Goodman, H. M., Nature, 286: 684–687 (1980)

Fife, K and Bower, M, *Br. J Cancer* 73:1317–1322 (1996)

Hudson, D., J. Org. Chem. 53:617–624, (1988)

Lee, A. C. J., et al., Mol. Immunol., 17:749 (1980)

Lee, et al., Mol Immunol 17:749–756, (1980)

Triozzi P L, and Stevens V C, Oncol Rep 6(1):7–17, 1999

Triozzi P L, et al., Clin Cancer Res 3(12 Pt 1): 2355–62, 1997

BACKGROUND OF THE INVENTION

Vaccination is a means for preparing the immune system to reduce disease symptoms, prevent horizontal transmission of infectious agents and reduce disease mortality. It is well known that the immune system of a subject will generate an immune response to foreign antigens. It is also known to confer immunity on an animal by administering an antibody formed elsewhere (i.e. passive immunization).

Standard vaccines include the administration of carbohydrates, peptides, polypeptides, and glycosylated polypeptides against which an immune response is desired (active immunization). Alternatives to vaccine administration include the administration of pre-formed antibodies to one or more peptide or polypeptides (passive immunization). Although polyclonal and monoclonal antibodies are readily produced by routine techniques, until recently, production and purification of safe antibody compositions has been relatively expensive and time consuming.

Historically, there have been serious limitations to the use of passive immunization procedures for human therapy. These limitations are most evident in the treatment of chronic diseases such as cancer due to the cost of antibody production and the requirement for prolonged administration of these antibodies. Additional difficulties are encountered when the immunogen is a soluble protein or an endogenous protein not normally recognized by the immune system of the subject.

Certain cancers are highly resistant to attack by the immune system of a host, even though in theory the host should mount an immune response against the cancer. It is believed that this resistance is due to the ability of the cancer to interfere with the normal immune response to the cancer cells, thereby allowing them to grow and proliferate.

Normally, Chorionic gonadotropin (CG), e.g. human chorionic gonadotropin (hCG), is secreted by cells of the human placenta and blastocyst. However, many human cancers produce and retain and/or secrete hCG at some point during carcinogenesis. hCG has been detected in the membranes of a variety of human cancer cell lines (Acevedo, et al., 1992), and in the serum of cancer patients (Braunstein, 1990). In fact, the hCG beta subunit C-terminal peptide (CTP) is highly expressed by a variety of cancers, and immunization with this construct has demonstrated antitumor activity in preclinical studies (Acevedo, et al., 1992; Acevedo, et al., 1987)).

For example, it has been demonstrated that hCG and/or its subunits are made by human lung cancer cells and that the hCG polypeptide or portions of it act as autocrine growth promoters for the tumor cells. (See, e.g., Rivera et al., 1989.) Additional references also describe that the active production of anti-hCG antibodies in tumor-bearing animals can result from administration of an hCG vaccine. (See, e.g., U.S. Pat. Nos. 5,762,931 and 4,780,312.).

Several biological activities associated with the ability of cancer cells to proliferate have been attributed to hCG including; (1) a link to tumor anergy (the lack of the immune response to tumors), (2) enhancement of tumor blood supply, and (3) the observation that hCG acts as a growth stimulatory factor for many cancer cells.

Epidemiological surveys indicate that human lung cancers are often associated with synthesis of hormones, predominantly human chorionic gonadotropin (hCG). Increased circulating levels of hCG and its subunits are often used as biochemical markers for malignancy, and decreased levels of hCG used as markers for successful surgery in human lung tumors. Free and/or tumor-associated β-hCG has been detected in bladder, pancreatic, cervical, colorectal, lung, pancreatic, esophageal breast, gastric, prostate, ovarian, uterine, cervical, and endometrial cancers, in addition to a majority of patients with germ cell tumors. (See, e.g., Dirnhofer, et al., 1998; Triozzi P L and Stevens V C, 1999). hCG and other gonadotropic hormones have also been associated with Kaposi's Sarcoma (K S, Fife, K and Bower, M, 1996).

Colorectal cancer is a disease that kills nearly half of those afflicted within 5 years of initial diagnosis and approximately one in 17 Americans develop colorectal cancer during their lifetime. Surgical intervention is not an option for most patients with advanced metastatic colorectal cancer. Initial chemotherapy with fluorouracil (5-FU) and leucovorin has become the standard for patients with stage III colon cancer (NIH Consensus Conference. Adjuvant therapy for patients with colon and rectal cancer. *JAMA* 264: 1444–1450, 1990; Goldberg R M and Erlichman C. *Oncology* 12: 59–63, 1998). Therapy for patients with 5-FU-refractory advanced colorectal cancer is currently irinotecan (Van Cutsem E and Blijham G H. *Semin Oncol* 26:. 13–20, 1999 and Cunningham D et al. *Lancet* 352: 1413–1418, 1998). Multiple new approaches to the treatment of advanced colorectal cancer include: (a) new drugs such as oxaplatin, capecitabine, uracil/tegafur (UFT), (Punt C J., *Cancer* 1998; 15: 679–689, 1998); (b) passive immunotherapy using a monoclonal antibody, 17-1A (Punt C J., 1998); and (c) several approaches to active specific immunotherapy (ASI) with one or more cancer-associated antigens (Goydos J S et al. *J Sur Res* 1996; 63: 298–304 and Vermorken, J B et al. *Lancet* 1999; 353: 345–350).

Several Ohio State patents to Stevens, e.g., U.S. Pat. Nos. 4,767,842, 4,855,285, 5,817,753 and 5,698,201, expressly incorporated by reference herein, disclose the use of a beta-hCG/tetanus toxoid modified peptide as an anti-cancer strategy based on antibody production against hCG by the host.

Although various research efforts are directed to improved methods for treatment of hCG-expressing cancers, there remains a need for an effective and safe method for reducing or eliminating the level of circulating CG and cell-associated CG in cancer patients with CG-expressing tumors.

SUMMARY OF THE INVENTION

It is therefore a general object of the invention to provide methods for immunotherapy of cancers which express human chorionic gonadotropin (hCG), or an immunogenic epitope thereof.

The invention relates to methods of eliciting an immune response against hCG by administering an hCG immunogenic peptide vaccine composition to a subject, particularly a human cancer patient, as a means to diminish, prevent the spread of, and/or progression of cancer.

The invention also relates to a human monoclonal antibody composition specifically immunoreactive with a 21 mer N-terminal fragment of hCG-CTP37 (hCG-CTP21, SEQ ID NO:4) alone, or in combination with a human monoclonal antibody specifically immunoreactive with a 16 mer C-terminal fragment of hCG-CTP37 (hCG-CTP16, SEQ ID NO:6).

Such human monoclonal antibody compositions may be prepared in a solution suitable for injection in a human patient and find utility in passive immunotherapy, particularly immunotherapy of cancer.

In one aspect, the invention provides a method for immunotherapy of cancer by administering a human monoclonal antibody composition 1 to 2 times per week for a period of at least 4 to 6 weeks, at dose of from about 25 to 500 mg.

In a related aspect, a human monoclonal antibody composition is administered together or sequentially with an hCG immunogenic peptide vaccine, derivatized to a suitable carrier protein. In one approach, the peptide vaccine is hCG-CTP37 (SEQ ID NO:2), alone or in combination with the hCG "loop" peptide (SEQ ID NO:9).

In another embodiment, the invention provides a method for classifying the immune response to hCG in a patient, by measuring the levels of patient anti-hCG antibodies specific to hCG-CTP16 (SEQ ID NO:6), hCG-CTP21 (SEQ ID NO:4), and hCG-CTP37 (SEQ ID NO:2), respectively, and classifying the patient into one of the following four groups, depending on the relative antibody levels, as follows, (1) patients in which neither anti-CTP16 nor anti-CTP21 antibodies, nor total anti-hCG-CTP37 antibodies are detectable (non-antibody responders); (2) patients in which in which total anti-hCG-CTP37 antibodies are detectable while neither first nor second antibodies are detectable (poor antibody responders); (3) patients having a detectable level of first antibodies, but undetectable levels of second antibodies (CTP16 only antibody responders); and (4) patients having detectable levels of both first and second antibodies (CTP16 and CTP21 antibody responders).

The invention further provides an improved method of treating a cancer patient population that fails to respond to an hCG-CTP37 vaccine dose of at least 1 mg peptide per administration, as evidenced by a negligible improvement in the patient's condition. The assay is typically carried out between 9–15 weeks after an initial vaccination, and if the patient's measured level of anti-hCG-CTP21 antibodies is undetectable or substantially lower than that of anti-hCG-CTP16 antibodies, further treating the patient by a vaccination regimen selected from one or more of: (i) successive, spaced administrations of hCG-CTP37 at a dose which is greater than that provided in the initial administration; (ii) successive, spaced administrations of hCG-CTP37 at a dose corresponding to less than 1 mg CTP37 peptide/patient/administration; (iii) successive, spaced administrations of a promoter vaccine composed of hCG loop peptide (SEQ ID NO:9) derivatized to a suitable carrier, in combination with the hCG-CTP37 (SEQ ID NO:2) vaccine; (iv) successive, spaced administrations of a promoter vaccine composed of hCG loop peptide (SEQ ID NO:9) derivative to a suitable carrier, followed by successive spaced administrations of the hCG-CTP37 (SEQ ID NO:2) vaccine, at a dose of the latter vaccine of less than less than 1 mg CTP37 peptide/patient/administration; (v) successive spaced administration of a CTP37 N-terminal peptide vaccine composed of hCG-CTP21 (SEQ ID NO:4), derivatized to a suitable carrier protein; (vi) successive, spaced administrations of a human monoclonal antibody specifically immunoreactive with hCG-CTP21 (SEQ ID NO:4) at least once every 1 to 2 weeks; (vii) successive, spaced administrations of a human monoclonal antibody specifically immunorcactive with hCG-CTP21 (SEQ ID NO:4) together with a human monoclonal antibody specifically immunoreactive with hCG-CTP16 (SEQ ID NO:6), at least once every 1 to 2 weeks; and (viii) successive spaced administrations of an hCG-CTP37 vaccine in combination with a human monoclonal antibody specifically immunoreactive with hCG-CTP21 (SEQ ID NO:4).

In a related aspect of this embodiment, the invention provides a diagnostic device and method for monitoring the immune response to hCG, which includes an hCG-CTP16 peptide, an hCG-CTP21 peptide, and an hCG-CTP37 peptide together with a reagent means for labeling human antibodies that are immunoreactive with the peptides and a detectable reporter.

These and other objects and features of the invention will be more fully appreciated when the following detailed description of the invention is read in conjunction with the accompanying drawings.

BRIEF DESCRIPTION OF THE FIGURES

FIG. 1 depicts the amino acid sequence of the beta subunit of human chorionic gonadotropin (hCG) as provided in GenBank Accession number 180437, designated SEQ ID NO:1.

FIG. 2A depicts residues 129–165 of the beta subunit of hCG (C-terminal peptide CTP, SEQ ID NO:2).

FIG. 2B depicts the C-terminal peptide (CTP, SEQ ID NO:3) of hCG, with an added N-terminal methionine.

FIG. 2C depicts residues 130–150 of the amino acid sequence of the beta subunit of hCG (C-terminal epiotope, CTP-21, SEQ ID NO:4).

FIG. 2D depicts residues 131–138 of the amino acid sequence of the beta subunit of hCG (epitope within CTP-21, SEQ ID NO:5).

FIG. 2E depicts residues 150–165 of the amino acid sequence of the beta subunit of hCG (N-terminal epitope, CTP-16, SEQ ID NO:6).

FIG. 2F depicts residues 150–165 of the amino acid sequence of the beta subunit of hCG (N-terminal epitope with added N-terminal C, CTP-17, SEQ ID NO:7).

FIG. 2G depicts residues 153–165 of amino acid sequence of the beta subunit of hCG (epitope within CTP-16, SEQ ID NO:8).

FIG. 2H depicts amino acids 58–77 of the beta subunit of hCG, the "loop" peptide SEQ ID NO:9).

DETAILED DESCRIPTION OF THE INVENTION

I. Definitions

Figure 3:
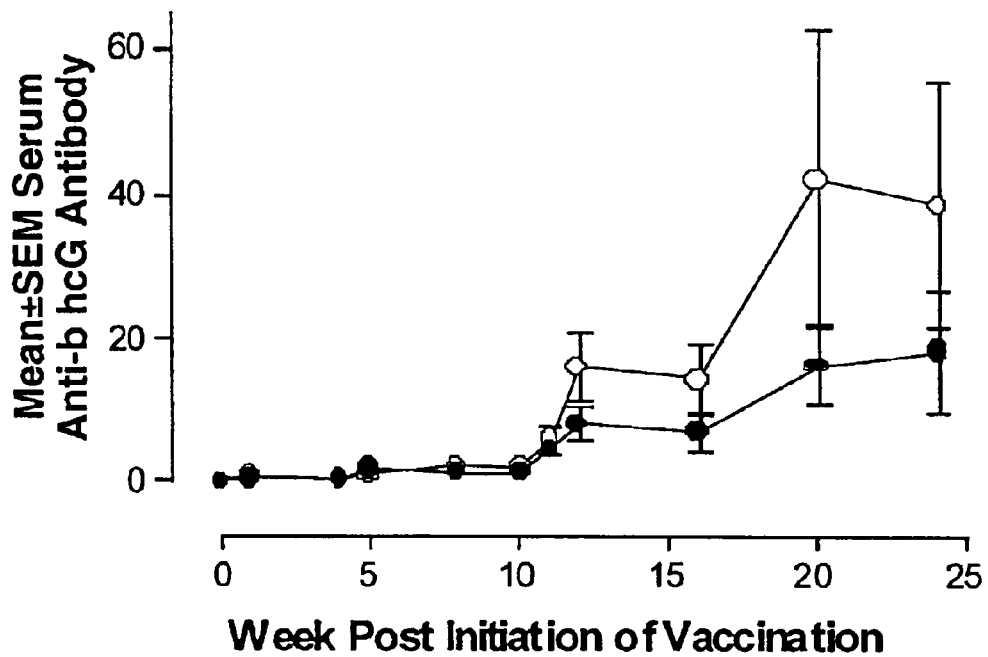
FIG. 3 represents the average level of anti β-hCG antibodies detected in the serum of colorectal cancer patients in a Phase II clinical trial over 0 to 24 weeks post initiation of vaccination with the C-terminal peptide of hCG. Patients received either a "high" or "low" dose of hCG. The high dose group (open circles) received an initial injection of 2.0 mg CTP37-DT, with a 1.0 mg booster injection of CTP37-DT at either 3 or 4 weeks, followed by a 1.0 mg booster of CTP37-DT every 3 months thereafter, and the low dose group (closed circles) received an initial injection of 0.5 mg CTP37-DT, with a 0.5 mg booster injection of CTP37-DT at either 3 or 4 weeks, followed by a booster of CTP37-DT every 3 months thereafter.

The term "hCG peptide", "hCG immunogenic peptide" or "hCG epitope" means an hCG peptide which has an amino acid sequence which is the same as part of, but not all of, the amino acid sequence of the entire hCG protein, and which retains at least one biological function or activity of the entire hCG protein, for example, a fragment which retains an immunological activity of the full hCG protein.

The term "hCG immunogenic peptide" or "hCG immunogenic beta subunit peptide" or fragments thereof, as used herein, refers to amino acid sequences derived from hCG or the beta subunit of hCG, respectively, which are capable of eliciting a cellular and/or humoral immune response when administered to a subject.

The terms "antigenic precursor" or "precursor" relative to hCG immunogenic peptides, as used herein refers to hCG peptides capable of being processed to hCG immunogenic peptides by the subject.

The term "hCG C-terminal peptide" or "hCG CTP37" as used herein refers to the C-terminal 37 amino acids of the beta subunit of hCG ("CTP37 mer ", FIG. 2A, SEQ ID NO:2), presented as the native sequence, or a variant or analog thereof, which has equivalent biological activity.

In some cases, the hCG CTP has an added methionine at the N-terminus (termed the "CTP38-mer", FIG. 2B, SEQ ID NO:3).

The term "loop" peptide, as used hereon with reference to hCG means amino acids 58 to 77 of the beta subunit of hCG (FIG. 2H, SEQ ID NO:9), wherein amino acids 58 and 77 are linked by a disulfide bridge, in the form of the native sequence, or a variant or analog thereof, which has equivalent biological activity.

The term "16 mer" or "C-terminal epitope", as used herein with reference to hCG means amino acids 150–165 of the beta subunit of hCG (FIG. 2E, SEQ ID NO:6), presented as the native sequence, or a variant or analog thereof, which has equivalent biological activity.

The term "17 mer", as used herein with reference to hCG means amino acids 150–165 of the beta subunit of hCG (FIG. 2F, SEQ ID NO:7), with an added C-terminal cysteine for purposes of derivatization to a carrier protein.

The term "21 mer" or "N-terminal epitope", as used herein with reference to hCG means amino acids 130 to 150 of the beta subunit of hCG (FIG. 2C, SEQ ID NO:4), presented as one native sequence, or a variant or analog thereof, which has equivalent biological activity.

The term "non-native" as used herein relative to an hCG immunogenic peptide or epitope, means the amino acid sequence of the epitope differs by one or more amino acids from the amino acid sequence of the same hCG immunogenic epitope as it is found in nature.

The "non-native" amino acid sequence may comprise an hCG immunogenic epitope having a variant amino acid sequence which contains one or more of "conservative" or "non-conservative" amino acid substitutions, amino acid insertions or deletions, or in some cases may have additional amino acids at the N- or C-terminal end of the peptide. Such a "non-native" hCG immunogenic peptide retains the biological activity (immunogenicity) of the native peptide from which it is derived.

The term "peptide carrier protein conjugate" is used interchangeably with the term "peptide derivatized to a carrier protein", and refers to an hCG immunogenic peptide which has been linked to a carrier protein to enhance its immunogenicity.

The term "hCG immunogenic peptide vaccine" or "hCG peptide vaccine", as used herein refers to an hCG immunogenic peptide derivatized to a suitable carrier molecule, as exemplified herein by hCG-CTP16 (SEQ ID NO:6) and hCG-CTP21 (SEQ ID NO:4).

The term "hCG vaccine" or "vaccine", as used herein refers to an hCG immunogenic peptide derivatized to a suitable carrier molecule, hCG-CTP37 (SEQ ID NO:2), and/or one or more passively administered anti-hCG human monoclonal antibodies.

The term "immune response" as used herein refers to a humoral immune response such as production of antibodies against an hCG immunogenic epitope or a cellular immune response such as a cytotoxic T cell response.

The term "immunocompetent subject", as used herein refers to a subject having immune response cells which upon exposure to an immunogenic epitope, is capable of mounting a cellular and/or humoral immune response against the immunogenic epitope.

The term immunogenic "epitope" or "antigenic determinant", as used herein relative to an hCG peptide refers to a portion of the hCG amino acid sequence which will generate a B- and/or T-cell mediated immune response against hCG. It is preferred that the epitope be unique; that is, an immune response generated to the specific hCG epitope shows little or no cross-reactivity with other antigens.

By "functional equivalent" is meant an amino acid sequence for an hCG immunogenic peptide having equivalent biological activity to the native sequence hCG immunogenic peptides described herein and presented as SEQ ID NOs:2, 4, 6 and 9. The relevant biological activity is immunological activity, i.e. the ability to elicit an immune response in a subject to whom the hCG immunogenic peptide vaccine is administered.

Amino acid residues are referred to herein by their standard single letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine.

The term "active immunization", as used herein is meant the use of hCG peptide vaccines to induce an immune response by the immune response cells of the subject.

The term "administering", as used herein means bringing the immune response cells of the subject in contact with an hCG immunogenic peptide vaccine. In most cases, such "administering", takes place either take by subcutaneous or intramuscular injection of the hCG immunogenic peptide vaccine composition into the subject.

The term "passive immunization", as used herein is meant the direct administration of antibodies to a subject as an immunization approach.

The term "adjuvant" is used herein refers to a substance which can elevate the total immune response of the subject to whom a vaccine is administered, i.e. by acting as a non-specific immunostimulator. An adjuvant can also be used to elicit an immune response more rapidly.

The term "successively spaced administrations" as used herein refers to treatment regimens of hCG immunogenic peptides vaccines which comprise an initial administration, followed by one or more "booster" administrations at various time intervals following the initial administration. The "booster" administrations may or may not be given at regularly spaced intervals.

As used herein, the terms "solution suitable for injection in a human patient", "in a form suitable for injection in a human patient" and "pharmaceutically acceptable", may be used interchangeably and refer to composition comprising carriers, diluents and reagents, capable of administration to a human subject without the production of adverse physiological effects.

The terms "treating", "treatment" and "therapy" as used herein refer to curative therapy, prophylactic therapy, and preventative therapy.

The term "dose" as used herein refers to the amount of anti hCG human monoclonal antibody or hCG immunogenic peptide vaccine administered to a patient. The amount varies with the subject, the immunogen and the presence of adjuvant, as described below.

The term "treatment efficacy potential" as used herein relative to treatment of cancer refers to the potential effectiveness of a given treatment strategy as determined by evaluation of various clinical endpoints including the immune response to hCG immunogenic peptides, tumor size and patient survival time.

As used herein, the term "fails to respond to the vaccine" generally means the patient has no detected immune response to hCG CTP37 or immunogenic epitopes thereof.

The term "body fluid" as used herein refers to a variety of sample types obtained from a subject including, urine, saliva, plasma, blood, spinal fluid, and other samples of biological origin.

As used herein, the term "analysis", relative to immunoassay of the immune response to hCG immunogenic peptides, may be an evaluation which is either qualitative (positive/negative) or quantitative.

II. Cancer and hCG

Although malignant tumors may express protein antigens that are recognized as foreign by a subject, and immune surveillance may limit the growth and spread of some types of tumors, the immune system does not effectively protect the subject from lethal human cancers.

Such tumors may overwhelm the immune system due to rapid growth and spread and/or the tumor cells may evade immune destruction. Proposed mechanisms for such evasion include, but are not limited to, (1) down-regulation of Class I MHC antigens on the surface of tumor cells resulting in little or no complexing of processed tumor peptide antigens with Class I MHC as required for recognition by cytotoxic T lymphocytes (CTL), (2) a lack of activation of CTL due to little or no expression of Class II MHC molecules by tumor cells such that they cannot directly activate tumor-specific CD4+ helper T cells (which produce signals likely to be needed for CTL activity), (3) a lack of co-stimulation cell surface markers that provide secondary signals for activation of CD4+ helper T cells, and (4) factors produced by tumor cells that suppress anti-tumor responses, such as fas-ligand. (Abbas, A K, et al., 1997)

Investigators have also determined, that certain polypeptides are supportive factors for and/or secreted by neoplastic cells in both man and other mammals. Such supportive factors have biochemical, biological and immunological similarity to hormones, particularly chorionic gonadotropin (CG). Certain carcinomas exude CG or an immunologically-similar material on their surfaces, thereby presenting to the immune system of the subject a surface which, superficially, appears to be formed of material endogenous to the subject and which is thus relatively non-immunogenic.

Free β-hCG (greater than 100 μg/ml) has been detected in bladder (47%), pancreatic (32%) and cervical cancer patients (30%), in addition to a majority of patients with germ cell tumors. Tumor-associated β-hCG has been detected in colorectal (52%), lung (34%), pancreatic (31%), esophageal (28%), breast (24%), and bladder (21%) cancers (Braunstein, 1990). In addition, immunohistochemical detection has been reported in approximately 8 to 19% of gastric, prostate, ovarian, uterine, cervical, and endometrial cancers. (Braunstein, 1990).

An effective treatment of malignant cancers must prevent further spread of neoplastic cells and reduce mortality, i.e. increase survival time for patients who have the disease. Current treatment methods including non-specific stimulation of the immune system, passive immunotherapy, and vaccination with killed tumor cells or tumor cell antigens, polypeptides or fragments thereof, alone or in combination with chemotherapy and/or radiation therapy.

Active immunization studies have indicated that a beta-hCG/tetanus toxoid modified polypeptide confers upon rats protection against an injection of tumor cells of the virulent rat mammary adenocarcinoma R 3230 AC, which is associated with CG-like material. Passive immunization has also resulted in protection against Lewis lung carcinoma tumors, viral-induced leukemia and a sarcoma tumor in mice (See, e.g., U.S. Pat. No. 5,698,201).

The C-terminal peptide of hCG, alone or in combination with the hCG "loop" peptide, injected intramuscularly, together with CRL 1005 (OPTIVAX™; Vaxcel Inc., Norcross, Ga.), as an adjuvant, has been evaluated in early phase clinical trials in patients with metastatic cancer. Measurable anti-hCG antibody production resulted in the studies, however, assessment of anti-cancer activity was not a component of the studies. [See, Triozzi P L and Stevens V C, Oncol Rep 6(1):7–17, 1999; Triozzi P L et al., Clin Cancer Res 3(12 Pt1):2355–62, 1997.]

III. Human Monoclonal Antibodies for Passive Immunotherapy

A. Production of Human Monoclonal Antibodies

The value and potential of antibodies for in vivo therapy has been long-recognized in the art. One approach has been to develop human or "humanized" monoclonal antibodies, which are not easily "recognized" as foreign by the patient in order to avoid an anti-antibody immune response. In some cases, the use of human B cell hybridoma-produced monoclonal antibodies have potential in the treatment of various disease conditions. However, many native human tumor antigens, are not immunogenic in humans and thus it may be difficult to isolate human B cells producing antibodies against human antigens.

Chimeric or "humanized" antibodies, are genetically engineered and assembled from portions of mouse and human antibody gene fragments. Such chimeric and humanized antibodies still retain a varying amount of the mouse antibody protein sequence and, accordingly, may trigger a human anti-mouse immune response when administered to a patient.

A recombinant DNA approach has focused on the production of chimeric antibodies having a human C[H] region and non-human (e.g., murine) antigen combining (variable) regions. These chimeric antibodies are generally produced by cloning the desired antibody variable region and/or constant region, combining the cloned sequences into a single construct encoding all or a portion of a functional chimeric antibody having the desired variable and constant regions, introducing the construct into a cell capable of expressing antibodies, and selecting cells that stably express the chimeric antibody.

Humanized forms of non-human (e.g., murine) antibodies are chimeric immunoglobulins, immunoglobulin chains or fragments thereof (such as Fv, Fab, Fab', F(ab')$_2$ or other antigen-binding sequences regions). Humanized antibodies include human antibodies in which residues from a complementary determining region (CDR) of a human antibody are replaced by residues from a CDR of a non-human species such as mouse, rat or rabbit. In most cases, the humanized antibody comprises variable region domains, in which all or substantially all of the CDR regions are of non-human origin. In some instances, Fv framework region (FR) residues of the human immunoglobulin are replaced by corresponding non-human residues. Methods for humanizing non-human antibodies are well known in the art (See, e.g., Jones, et al, 1986; Riechmann, et al., 1988; Verhoeyen, et al., 1988). In order to find utility in the methods of the invention, humanized antibodies must maintain high affinity for the peptide antigen and other favorable biological properties.

Human antibodies may also be produced using phage display libraries (Hoogenboom and Winter, 1991; Marks, et al., 1991).

Filamentous phage display vectors or "phagemids", have been repeatedly shown to allow the efficient preparation of large libraries of monoclonal antibodies having diverse and novel immunological specificities. The filamentous phage coat protein membrane anchor domain serves to link a gene-product and gene during the assembly stage of phage replication, and has been used for the cloning and expression of antibodies from combinatorial libraries. (See, e.g., Kang, et al., 1991). This technique provides completely human antibodies, which have no framework or CDR residues of rodent origin, such as are found in "humanized" antibodies.

The method for producing a human monoclonal antibody generally involves (1) cloning antibody V domain genes in-frame into either a major or minor coat protein gene of a filamentous bacteriophage, (2) expressing the assembled heterodimeric antibody molecule, such that functional antibody fragments are displayed on the surface of the phage particle, (3) isolating the surface-expressed phage particle using immunoaffinity techniques, resulting in selection of the gene encoding the antibody exhibiting those properties. (See, e.g., Hoogenboom, H R, et al., 1998; U.S. Pat. No. 5,804,440).

A repertoire of V genes from unimmunized human donors can be constructed and antibodies to a diverse array of antigens (including self-antigens) isolated using phage display (Marks et al., 1991; Griffiths, et al., 1993).

The affinity of human antibodies obtained by phage display can be improved by sequentially replacing the heavy and light chain V region genes with repertoires of naturally occurring variants of V domain genes obtained from unimmunized donors in order to select for higher affinity antibodies. (See, e.g., Griffiths and Duncan, 1998; Aujame, et al., 1997). The diversity of human antibodies obtained by phage display can also be increased by shuffling the heavy and light chain genes (Kang, et al., 1991), by altering the CDR3 regions of the cloned heavy chain genes (Barbas, et a., 1992), and by introducing random mutations into the library by polymerase chain reactions (PCR) (Gram, et al., 1992).

Alternatively, it is now possible to produce transgenic animals (e.g. xenomice) that are capable, upon immunization, of producing a full repertoire of human antibodies in the absence of endogenous immunoglobulin production. In this approach, large fragments of both the human heavy and light chain Ig genes have been inserted into the mouse germline to create a mouse strain capable of producing a broad repertoire of antigen-specific, fully human antibodies.

The xenomouse produces B cells expressing human heavy chain (h mu) and human K light chain (h K), or h mu and mouse lambda (m lambda) light chain. These mice produce significant levels of fully human antibodies with a diverse adult-like repertoire and, upon immunization with antigens, generate antigen-specific fully human monoclonal antibodies. (See, e.g., Jakobovits, et al., 1995; Jakobovits, 1995).

Such xenogenic mouse-derived human monoclonal antibodies may not have the correct Ig heavy chain for complement fixation in humans, e.g., IgG1. In such cases, the antibody encoding mRNA from the xenogenic mouse hybridoma may be used to obtain cDNA into which the cDNA for the IgG1 heavy chain is inserted. This cassette may then be inserted into an expression vector using procedures routinely employed by those of skill in the art, and subsequently for used in the production of transgenic goats. Transgenic goats have been developed wherein inducible promoters can trigger the expression of the protein encoded therein such that it is secreted into the milk of the goats. This procedure allows for relatively low cost production of large quantities of human monoclonal antibodies.

In a preferred approach, the anti-hCG immunogenic peptide antibodies of the invention comprise human antibodies, produced using xenogenic mouse technology, followed by IgG heavy chain replacement, cloned and expressed in transgenic goats, as described above.

B. Therapeutic Compositions Comprising Human Monoclonal Antibodies

The present invention therefore contemplates therapeutic compositions useful for practicing immunotherapy of cancer.

Therapeutic compositions containing one or more different human monoclonal antibodies specifically immunoreactive with an epitope of hCG CTP37 and the use thereof in the immunotherapy methods of the invention, are described herein. Preferred human monoclonal antibodies include anti hCG-CTP16 (SEQ ID NO:6) and anti hCG-CTP21 (SEQ ID NO:4).

A therapeutically effective amount of a human monoclonal antibody is an amount calculated to achieve the desired effect, i.e., to neutralize the hCG present in the serum or on the tumor cells of the patient, and thereby decrease the amount of detectable hCG or free hCG in the serum or on the tumor cells of the patient. Such a decrease is correlated with increased survival time for the patient.

The therapeutic compositions of the present invention contain a physiologically acceptable carrier, excipient, or diluent together with at least one species of human monoclonal antibody specifically immunoreactive with an epitope of hCG CTP37, dissolved or dispersed therein as an active ingredient, formulated according to conventional practice.

Therapeutic compositions for injection or infusion may take such forms as suspensions, solutions or emulsions of the antibody in oily or aqueous vehicles, and, may contain components such as suspending, stabilizing and/or dispensing agents. Alternatively, the composition may be in a dry form, for reconstitution before use with an appropriate sterile liquid.

The human monoclonal antibodies of the invention can be administered parentally by injection or by gradual infusion over time. In most cases, therapeutic compositions comprising the human monoclonal antibodies of the invention are administered intravenously, however, other delivery means are contemplated. For example, human monoclonal antibodies of the invention can be injected intravenously, intraperitoneally, intramuscularly, subcutaneously, intratumorally; or administered transdermally or by peristaltic means.

Suitable regimens for antibody administration are variable, but are typified by an initial administration followed by repeated doses at one or more intervals by subsequent administration. In the treatment methods of the invention, the anti-hCG antibodies may be administered together with or sequentially to, hCG immunogenic peptide vaccines.

A therapeutically effective amount of an antibody for use in the methods of this invention is typically an amount of antibody in a pharmaceutically acceptable composition that is sufficient to decrease the amount of detectable hCG in the patient.

The dosage can vary from about 25 mg to about 500 mg per patient per administration, wherein an average patient is 70 kg. In general, the anti-hCG antibodies are administered 1 to 2 times per week for a period of 4 to 6 weeks. However, in some cases, such antibody administration may be continued for an indefinite time period. The duration of antibody treatment is evaluated in conjunction with hCG immunogenic peptide vaccine administration based on the immune response of the patient to hCG-CTP16, hCG-CTP21 and hCG-CTP37, as further described below.

It will be understood that when the immunotherapy methods of the invention comprise the administration of a human monoclonal antibody specifically immunoreactive with hCG together with an hCG immunogenic peptide vaccine, the dose of human monoclonal antibody may be adjusted based on the results of an immunoassay for hCG immunogenic peptides, which is preformed beginning approximately 9 to 15 weeks post initial hCG vaccine administration.

More specifically, the levels of patient antibodies to a 16 mer C-terminal fragment of hCG-CTP37 (hCG-CTP16, SEQ ID NO:6), a 21 mer N-terminal fragment of hCG-CTP37 (hCG-CTP21, SEQ ID NO:4) and the entire hCG-CTP37 peptide (SEQ ID NO:2), are monitored at various times. The dosing regimen for passive hCG-CTP37 human monoclonal antibody administration is adjusted in combination with the hCG peptide vaccine dosing regimen, as needed, to result in detected antibodies to both hCG-CTP16 (SEQ ID NO:6) and hCG-CTP21 (SEQ ID NO:4) in a body fluid of the patient.

Preferably, the administration of an hCG vaccine results in a level of detected antibodies against hCG-CTP37 (SEQ ID NO:2), hCG-CTP16 (SEQ ID NO:6) and hCG-CTP21 (SEQ ID NO:4). Even more preferably, the hCG peptide vaccine administration results in a level of detected antibodies against both hCG-CTP16 (SEQ ID NO:6) and hCG-CTP21 (SEQ ID NO:4), wherein the immune response to both peptides is similar in magnitude.

IV. hCG Immunogenic Peptides as Vaccines

A. hCG Immunogenic Epitopes

An "hCG immunogenic epitope" or "hCG antigenic epitope" is any amino acid sequence, or combination of amino acid sequences which elicits an immune response against hCG.

In one preferred embodiment, an hCG vaccine comprises the C-terminal peptide (CTP37, SEQ ID NO:2), of the beta subunit of hCG, administered to a subject alone or in combination with one or more additional immunogenic hCG peptides and/or together with passive administration of one or more anti-hCG antibodies.

Preferred immunogenic epitopes for use in the methods of the present invention are the C-terminal 37 amino acids of the beta subunit of hCG (CTP37), and peptides derived therefrom, alone or in combination with amino acids 58 to 77 of the beta subunit of hCG (the "loop" peptide).

The "loop" peptide of the beta subunit of hCG is substantially similar to the corresponding region of human leutenizing hormone (LH), follicle stimulating hormone (FSH) and thyroid stimulating hormone (TSH). Accordingly, the "loop" peptide or an analog thereof is administered in conjunction with the CTP37 peptide an analog thereof, or peptides derived therefrom.

The combined administration of the "loop" and CTP37 peptides may be accomplished as follows: (1) the two peptides may be chemically linked or synthesized in tandem prior to derivatization to a suitable carrier protein; (2) both peptides may be chemically derivatized to the same carrier without first being chemically linked to one another; (3) the two peptides may be derivatized to separate carriers and a mixture of the two resultant conjugates administered to the subject to be treated; or (4) the two peptides may be derivatized to separate carriers and the two resultant conjugates administered separately to the subject to be treated.

The hCG vaccines described herein are representative of the types of hCG vaccines that can be used in the methods of the current invention to generate an immune response against two or more epitopes of hCG-CTP37. In general, the size of the peptide antigen must be at least large enough to encompass one or more immunogenic epitopes of hCG. The smallest useful immunogenic epitope or fragment anticipated by the present disclosure would generally be on the order of about 8 contiguous amino acid residues in length, with sequences on the order of about 8 to about 40 or more of amino acids being preferred.

Although the mechanism is not part of the invention, the present invention is based on the existence of two major epitopes within the carboxy terminal 37 amino acids of βhCG. Two epitopes within the carboxy terminal 37 amino acids of □hCG, have been previously described (Berger P et al. *Mol and Cell Endocrinol* 125: 33–43, 1996). FIGS. 2A, 2C and 2E show the amino acid sequences of CTP37, and two peptides found within CTP37, designated CTP21 and CTP16, respectively. In practicing the invention, an hCG vaccination strategy may comprise administration of one or more of CTP37, CTP21 and CTP16. However, studies described herein show that the immune response to the CTP16 epitope is immunodominant and accordingly, administration of CTP37 alone or in combination with CTP21 is preferred.

In general, the initial administration of an hCG immunogenic peptide vaccine consists of at least 1 mg of hCG-CTP37. Follow-up or "booster" administrations of hCG immunogenic peptide vaccines or passively administered anti-hCG antibodies, are usually provided to a cancer patient in successive, spaced administrations of one or more of the following: (i) a dose of the CTP37 vaccine (SEQ ID NO:2) which is greater than that provided in the initial administration; (ii) a dose of the vaccine corresponding to less than 1.0 mg CTP37 peptide per patient per administration; (iii) a promoter vaccine composed of the hCG loop peptide (SEQ ID NO:9), derivatized to a suitable carrier, in combination with the hCG-CTP37 vaccine; (iv) a promoter vaccine composed of the hCG loop peptide (SEQ ID NO:9), derivatized to a suitable carrier, followed by successive spaced administrations of the hCG-CTP37 vaccine, at a dose of the latter vaccine of less than less than 1.0 mg CTP37 peptide per patient per administration; (v) a peptide vaccine composed of hCG-CTP21 (SEQ ID NO:4), derivatized to a suitable carrier protein; (vi) passive administration of at least one dose every 1 to 2 weeks of a human monoclonal antibody specifically immunoreactive with a 21 mer N-terminal fragment of hCG-CTP37 (hCG-CTP21, SEQ ID NO:4); (vii) passive administration of at least one dose every 1 to 2 weeks of a human monoclonal antibody specifically immunoreactive with hCG-CTP21 (SEQ ID NO:4) in combination with a human monoclonal antibody specifically immunoreactive with hCG-CTP16 (SEQ ID NO:6); and (viii) successive spaced administrations of an hCG-CTP37 vaccine (SEQ ID NO:2) in combination with a human monoclonal antibody specifically immunoreactive with hCG-CTP21 (SEQ ID NO:4).

In one approach, the amount of the CTP37 component of the hCG vaccine is less than 1.0 mg, preferably 0.5 mg. In a related aspect, when the CTP37 vaccine is administered to a patient together with the "loop" vaccine, the amount of the CTP37 component of the hCG vaccine is less than 1.0 mg, preferably 0.5 mg, and the amount of the "loop" vaccine is equal to, or greater than that of the CTP37 peptide.

In all cases, the hCG immunogenic peptide is conjugated to a carrier molecule, e.g., a protein. In general, each hCG immunogenic peptide is separately conjugated to a carrier protein. When more than one conjugated hCG immunogenic peptide is included in the treatment regimen for a given patient, the hCG peptide vaccines may be administered to the patient at the same time, or at different times. In most cases, conjugated hCG immunogenic peptides are administered together, in successively spaced administrations.

B. Preparation of an hCG Peptide Vaccine

Various hCG polypeptide chains have been expressed, via recombinant DNA technology, in host cells such as bacteria, yeast, and cultured mammalian cells. (See, e.g., Fiddes, J. C. and Goodman, H. M., 1979) and (Fiddes, J. C. and Goodman, H. M., 1980) which describe the cloning of, respectively, the alpha and beta subunits of human chorionic gonadotropin (hCG).

The amino acid sequence of the beta subunit of hCG, available as GenBank Accession Number 180437, and presented herein as SEQ ID NO:1, was used to select peptides for use in the methods of the invention.

hCG immunogenic peptides were chemically synthesized using either Fmoc (9-fluorenylmethyloxycarbonyl) chemistry, essentially as described by D. Hudson, 1988, or Boc (tert-butyloxycarbonoyl) chemistry. Techniques for amino acid synthesis are routinely employed by those of skill in the art using currently available laboratory equipment (e.g., Applied Biosystems, Inc., Foster City, Calif.). Following synthesis, peptides are generally purified by HPLC, and the integrity and authenticity of the peptides determined by Edman degradation followed by traditional sequencing or mass-spectrophotometric analyses, e.g. NMR analysis of the intact peptide. The immunogenicity of each synthetic peptide is determined individually, through various in vitro immunoassays to determine immunoreactivity with antibodies in the body fluids, e.g., serum or plasma, taken from a subject known to have anti-hCG CTP37 antibodies.

C. Variant or Modified hCG Immunogenic Peptides

In most cases, hCG immunogenic peptides used in the methods of the invention have the same sequence as native hCG immunogenic peptides. However, in some cases, hCG immunogenic peptides are variant hCG peptides.

Some substitution of amino acids is possible without effecting the immunogenic character of the fragment.

Standard substitution classes are the six classes based on common side chain properties and highest frequency of substitution in homologous proteins in nature, as determined, for example, by a standard Dayhoff frequency exchange matrix (Dayhoff). These classes are Class I: Cys; Class II: Ser, Thr, Pro, Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and a halogenated tyrosine in Group VI. Further, the classes may include both L and D stereoisomers, although L-amino acids are preferred for substitutions.

Once an amino acid substitution or modification is made, the variant hCG immunogenic peptide is screened immunogenicity, in an in vitro immunoassay.

The amino acid sequences of hCG immunogenic peptides described herein may include additional residues, such as additional N- or C-terminal amino acids, and yet still be essentially the same as one of the sequences disclosed herein, so long as the peptide or polypeptide maintains the appropriate biological activity, e.g. immunogenicity.

The amino acids of an hCG immunogenic peptide may be changed in a manner to create an equivalent, or even an improved molecule. It is the immunogenicity of the hCG peptide which defines its biological activity. Certain amino acid sequence substitutions can be made in the amino acid sequence and the nucleic acid sequence encoding it, resulting in expression of an hCG peptide with greater biological utility or activity (immunogenicity). In some case such changes may provide other benefits, e.g., stability or more desirable pharmacologic properties with maintenance of equivalent biological utility and activity.

In making such changes, the hydropathic index of amino acids may be considered. Certain amino acids may be substituted by other amino acids having a similar hydropathic index or score and still obtain a biological functionally equivalent protein. (Kyte and Doolittle, 1982). In making such changes, the substitution of amino acids whose hydropathic indices are within +/−2 is preferred, those which are within +/−1 are particularly preferred, and those within +/−0.5 are even more particularly preferred. It is also understood in the art that the substitution of like amino acids can be made effectively on the basis of hydrophilicity. U.S. Pat. No. 4,554,101. In such changes, the substitution of amino acids whose hydrophilicity values are within +/−2 is preferred, those which are within +/−1 are particularly preferred, and those within +/−0.5 are even more particularly preferred.

Variant hCG immunogenic peptides for use in the methods of the invention may have improved properties for administration to patients, however, such peptides retain the immunogenicity of the native sequence hCG immunogenic peptides described herein.

V. Treatment Regimens for Generating an Anti-hCG Immune Response

A. In vivo Administration

In vivo administration of hCG vaccines may be achieved by inoculation in the presence of adjuvants or other substances that have the capability of recruiting immune system cells to the site of the inoculation. An hCG immunogenic peptide vaccine may be administered alone or in combination with passively administered human monoclonal antibodies which are specifically immunoreactive with a 16 mer C-terminal fragment of hCG-CTP37, e.g., hCG-CTP16, SEQ ID NO:6; and/or hCG-CTP21, SEQ ID NO:4.

In the methods of the invention, the immune response cells of a subject in whom protective immunization is desired, are exposed to an hCG immunogenic peptide vaccine alone or in combination with one or more human monoclonal antibodies which are specifically immunoreactive with an epitope of hCG CTP37. Protective immunization can be achieved following such exposure by effecting a reduction in the amount of circulating hCG or tumor-associated hCG in the subject. Both antibody- and cell-mediated immune responses may contribute to the anti-cancer activity of hCG vaccines.

In the methods of the invention, an hCG immunogenic peptide vaccine and/or human monoclonal antibody is administered in a manner compatible with the dosage formulation, and in an amount that is immunogenic and therapeutically effective. The quantity to be administered depends on the subject to be treated, including, e.g., the capacity of the individuals' immune system to respond to a peptide vaccine.

In general, the immunotherapeutic methods of the present invention are applicable to subject who already has cancer. This means the subject has been diagnosed as having cancer by one or more criteria employed by those of skill in the art to diagnose the relevant type of cancer. One such criteria is that the cancer is characterized by expression of hCG on the surface of the cancer cells and in some cases further characterized by the presence of circulating hCG in the plasma and/or other bodily fluids of the patient. Exemplary types of cancers, include, colorectal cancer, pancreatic cancer, breast cancer, lung cancer, and testicular cancer which is refractile to treatment with cisplatin.

In some cases, the immunotherapeutic methods of the invention are applicable to a subject who is at high risk for developing cancer, or for whom one or more diagnostic criteria indicate that cancer may be developing.

Surgery, radiation therapy, and chemotherapy are currently the primary methods for cancer treatment. It is comtemplated that passive immunization with anti-hCG CTP37 human monoclonal antibodies and/or hCG peptide vaccine-based treatment may be combined with such other cancer therapies. It will be appreciated that the methods described herein may interact in synergistic or additive ways with any one of surgery, radiation therapy, and chemotherapy, resulting in a greater therapeutic effect. In some cases, improved methods for treating cancer will combine conventional cancer treatments, e.g. chemotherapy or radiation therapy, together with passive immunization by administration of anti-hCG CTP37 human monoclonal antibodies and/or administration of hCG peptide vaccines.

B. hCG Peptide Vaccine Compositions

The invention provides a method of inducing an immune response against the C-terminal peptide of the beta subunit of hCG, a peptide which is itself substantially non-immunogenic. This is accomplished by conjugating the peptide with a carrier molecule prior to administration to a subject.

In the methods of the invention, an immunologically effective amount of one or more hCG immunogenic peptides derivatized to a suitable carrier molecule, e.g., a protein is administered to a cancer patient by successive, spaced administrations of a vaccine composed of an hCG immunogenic peptide or peptides conjugated to a carrier molecule, in a manner effective to result in an improvement in the patient's condition.

In a preferred embodiment, hCG immunogenic peptides are coupled to one of a number of carrier molecules, known to those of skill in the art. A carrier protein must be of sufficient size for the immune system of the subject to which it is administered to recognize its foreign nature and develop antibodies to it.

In some cases the carrier molecule is directly coupled to the hCG immunogenic peptide. In other cases, there is a linker molecule inserted between the carrier molecule and the hCG immunogenic peptide.

In one exemplary embodiment, the coupling reaction requires a free sulfhydryl group on the peptide. In such cases, an N-terminal cysteine residue is added to the peptide when the peptide is synthesized. For example, CTP17 (SEQ ID NO:7) has the same sequence as the hCG beta subunit peptide, CTP16 (SEQ ID NO: 6), plus an added N-terminal cysteine residue which facilitates coupling of CTP16 to a carrier molecule.

In an exemplary embodiment, traditional succinimide chemistry is used to link the peptide to a carrier protein. Methods for preparing such peptide:carrier protein conjugates are generally known to those of skill in the art and reagents for such methods are commercially available (e.g., from Sigma Chemical Co.). Generally about 5–30 peptide molecules are conjugated per molecule of carrier protein.

Exemplary carrier molecules include proteins such as keyhole limpet hemocyanin (KLH), bovine serum albumin (BSA), flagellin, influenza subunit proteins, tetanus toxoid (TT), diphtheria toxoid (DT), cholera toxoid (CT), a variety of bacterial heat shock proteins, glutathione reductase (GST), or natural proteins such as thyroglobulin, and the like. One of skill in the art can readily select an appropriate carrier molecule.

In a preferred embodiment an hCG immunogenic peptide is conjugated to diphtheria toxin (DT).

In some cases, the carrier molecule is a non-protein, such as Ficoll 70 or Ficoll 400 (a synthetic copolymer of sucrose and epichlorohydrin), a polyglucose such as Dextran T 70.

The degree of conjugation must be adequate to induce an immune response by a cancer patient at a level sufficient to neutralize some or all of the effects of hCG associated with the patient's condition. It will be appreciated that this will vary dependent upon the peptide, the carrier molecule and the patient.

The invention provides hCG vaccine compositions as above-described wherein each hCG immunogenic peptide is coupled to the same or a different carrier protein.

An hCG vaccine composition may comprise single or multiple copies of the same or different hCG immunogenic peptide, coupled to a selected carrier molecule. In one aspect of this embodiment, the hCG vaccine composition may contain different hCG immunogenic peptides with or without flanking sequences, combined sequentially into a polypeptide and coupled to the same carrier. Alternatively, the hCG immunogenic peptides, may be coupled individually as peptides to the same or a different carrier, and the resulting hCG immunogenic peptide-carrier conjugates blended together to form a single composition, or administered individually at the same or different times.

For example, hCG immunogenic peptides may be covalently coupled to the diphtheria toxoid (DT) carrier protein via the cysteinyl side chain by the method of Lee A. C. J., et al., 1980, using approximately 15–20 peptide molecules per molecule of diphtheria toxoid (DT).

In general, derivatized hCG peptide vaccine compositions are administered with a vehicle. The purpose of the vehicle is to emulsify the vaccine preparation. Numerous vehicles are known to those of skill in the art, and any vehicle which functions as an effective emulsifying agent finds utility in the methods of the invention. One preferred vehicle for administration comprises a mixture of mannide monooleate with squalane and/or squalene. Squalene is preferred to squalane for use in the vaccines of the invention, and preferably the ratio of squalene and/or squalane per part by volume of mannide monooleate is from about 4:1 to about 20:1.

To further increase the magnitude of the immune response resulting from administration of the hCG vaccine, an immunological adjuvant is included in the vaccine formulation. Exemplary adjuvants known to those of skill in the art include water/oil emulsions, non-ionic copolymer adjuvants, e.g., CRL 1005 (OPTIVAX™; Vaxcel Inc., Norcross, Ga.), aluminum phosphate, aluminum hydroxide, aqueous suspensions of aluminum and magnesium hydroxides, bacterial endotoxins, polynucleotides, polyelectrolytes, lipophilic adjuvants and synthetic muramyl dipeptide (norMDP) analogs. Preferred adjuvants for inclusion in an hCG vaccine composition for administration to a patient are norMDP analogs, such as N-acetyl-nor-muranyl-L-alanyl-D-isoglutamine, N-acetyl-muranyl-(6-0-stearoyl)-L-alany-D-isoglutamine, and N-Glycol-muranyl-L.alphaAbu-D-isoglutamine (Ciba-Geigy Ltd.). In most cases, the mass ratio of the adjuvant relative to the peptide conjugate is about 1:2 to 1:20. In a preferred embodiment, the mass ratio of the adjuvant relative to the peptide conjugate is about 1:10. It will be appreciated that the adjuvant component of the hCG vaccine may be varied in order to optimize the immune response to the hCG immunogenic epitopes therein.

Just prior to administration, the hCG immunogenic peptide carrier protein conjugate and the adjuvant are dissolved in a suitable solvent and an emulsifying agent or vehicle, is added. For example, an hCG immunogenic peptide carrier protein conjugate composition may include the CTP37 peptide conjugated to DT dissolved in phosphate buffered saline (PBS) together with norMDP, and further containing a squalene/mannide monooleate emulsifying agent.

Suitable pharmaceutically acceptable carriers for use in an immunogenic proteinaceous composition of the invention are well known to those of skill in the art. Such carriers include, for example, phosphate buffered saline, or any physiologically compatible medium, suitable for introducing the hCG vaccine into a subject.

Numerous drug delivery mechanisms known to those of skill in the art may be employed to administer the hCG immunogenic peptides and of the invention. Controlled release preparations may be achieved by the use of polymers to complex or absorb the peptides or antibodies in the methods of the present invention. Controlled delivery may accomplished using macromolecules such as, polyesters, polyamino acids, polyvinyl pyrrolidone, ethylenevinylacetate, methylcellulose, carboxymethylcellulose, or protamine sulfate, the concentration of which can alter the rate of release of the peptide vaccine.

In some cases, the hCG peptides may be incorporated into polymeric particles composed of e.g., polyesters, polyamino acids, hydrogels, polylactic acid, or ethylene vinylacetate copolymers. Alternatively, the hCG peptide vaccine is entrapped in microcapsules, liposomes, albumin microspheres, microemulsions, nanoparticles, nanocapsules, or macroemulsions, using methods generally known to those of skill in the art.

C. Treatment Regimens

The hCG vaccines of the invention may be administered by routes including, but not limited to, intradermal (ID) injection, intramuscular (IM) injection, subcutaneous (SC) injection, intravenous (IV) injection, intraperitoneal (IP) injection, and peritumoral injection. The preferred route of administration is subcutaneous (SC) injection.

In the cancer treatment methods of the invention, a patient is given an initial administration of less than 2.0 mg hCG-CTP37 (SEQ ID NO:2) and preferably less than 1.0 mg hCG-CTP37 derivatized to a suitable carrier molecule, in a pharmaceutically acceptable composition. In some cases, the initial vaccine comprises the combination of less than 2.0 mg hCG-CTP37 (SEQ ID NO:2), together with less than 2.0 mg hCG-"loop" peptide (SEQ ID NO:9), wherein each hCG immunogenic peptide is separately derivatized to a suitable carrier molecule. In one preferred embodiment, a patient is given an initial vaccine composed of the combination of 0.5 mg hCG-CTP37 (SEQ ID NO:2), together with 0.5 mg hCG "loop" peptide (SEQ ID NO:9).

After a period of between 9 to 15 weeks post initial vaccination, the level of patient antibodies to a 16 mer C-terminal fragment of hCG-CTP37, an 21 mer N-terminal fragment of hCG-CTP37 and hCG-CTP37 are evaluated in an immunoassay. The immunoassay may be repeated at regular intervals prior to, during and following anti-cancer treatment.

Dependent upon the immunoassay result, the hCG vaccine treatment regimen may be adjusted in order to optimize the immune response to hCG. A preferred dosing regimen will result in a patient immune response to both the 16 mer C-terminal peptide fragment and 21 mer N-terminal peptide fragment of hCG-CTP37, with a similar magnitude of immune response to both peptides, which is detectable beginning 9 to 15 weeks after an initial vaccine administration.

It is preferred that the immune response to CTP21 (SEQ ID NO:4), be detectable, and more preferable that the detected immune response to CTP21 be of similar magnitude to the immune response to CTP16 (SEQ ID NO:6). By "similar magnitude", is meant, the detected immune response to CTP21 and CTP16 does not differ by more than 50%, preferably by not more than 20%. In other words, the immune response to CTP21 (SEQ ID NO:4) is not substantially lower than the immune response to CTP16 (SEQ ID NO:6).

A patient's immune response to hCG may be grouped as follows:

(1) patients with no detectable anti-CTP37 antibody in their plasma (non-antibody responders); (2) patients in which total anti-hCG-CTP37 antibodies are detectable while neither anti-CTP16 or anti-CTP21 antibodies are detectable (poor antibody responders); (3) patients with detectable anti-CTP37 antibody and anti-CTP16 antibody, but no detectable anti-CTP21 antibody in their plasma (CTP16 only antibody responders); and (4) patients with detectable anti-CTP37, anti-CTP16 and anti-CTP21 antibody in their plasma (CTP16 and CTP21 antibody responders).

Following immunoassay, patients in Groups (1), (2), (3) and patients in Group (4) wherein the level of antibody specific to the CTP21 N-terminal fragment is substantially lower than the level of antibody specific to the CTP16 C-terminal fragment of hCG-CTP37, may be treated with a vaccination regimen selected from one or more of the following: (i) successive, spaced administrations of the hCG-CTP37 (SEQ ID NO:2) vaccine at a dose which is greater than that provided in the initial administration; (ii) successive, spaced administrations of the hCG-CTP37 (SEQ ID NO:2) vaccine at a dose corresponding to less than 1 mg CTP37 peptide/patient/administration; (iii) successive, spaced administrations of a promoter vaccine composed of hCG loop peptide (SEQ ID NO:9) derivatized to a suitable carrier, in combination with the hCG-CTP37 (SEQ ID NO:2) vaccine; (iv) successive, spaced administrations of a promoter vaccine composed of hCG loop peptide (SEQ ID NO:9) derivative to a suitable carrier, followed by successive spaced administrations of the hCG-CTP37 (SEQ ID NO:2) vaccine, at a dose of the latter vaccine of less than less than 1 mg CTP37 peptide/patient/administration; (v) successive spaced administration of a CTP37 N-terminal peptide vaccine composed of hCG-CTP21 (SEQ ID NO:4), derivatized to a suitable carrier protein; (vi) successive, spaced administrations of a human monoclonal antibody specifically immunoreactive with hCG-CTP21 (SEQ ID NO:4) at least once every 1 to 2 weeks; (vii) successive, spaced administrations of a human monoclonal antibody specifically immunoreactive with hCG-CTP21 (SEQ ID NO:4) together with a human monoclonal antibody specifically immunoreactive with hCG-CTP16 (SEQ ID NO:6), at least once every 1 to 2 weeks; and (viii) successive spaced administrations of an hCG-CTP37 vaccine in combination with a human monoclonal antibody specifically immunoreactive with hCG-CTP21 (SEQ ID NO:4).

Following immunoassay, patients in Group (4), wherein the level of antibody specific to the CTP21 N-terminal fragment is similar in magnitude to the level of antibody specific to the CTP16 C-terminal fragment of hCG-CTP37, may also be treated with a vaccination regimen selected from one or more of (i) through (viii), detailed above.

Preferably, the administration of an hCG vaccine results in a level of detected antibodies against hCG-CTP37 (SEQ ID NO:2), hCG-CTP16 (SEQ ID NO:6) and hCG-CTP21 (SEQ ID NO:4). Even more preferably, the hCG peptide vaccine administration results in a level of detected antibodies against both hCG-CTP16 (SEQ ID NO:6) and hCG-CTP21 (SEQ ID NO:4), wherein the immune response to both peptides is similar in magnitude.

It will be understood that the treatment regimens described above, are presented for exemplary purposes and that the treatment regimen may be adjusted as needed, dependent upon the patient's immune response to hCG, as detailed above. One aspect of the present invention is directed to the intermittent monitoring of the immune response to hCG-CTP37, hCG-CTP21 and hCG-CTP16, and a corresponding adjustment in the treatment regimen based on the results of such monitoring.

D. Dose Ranges

Prior to the present invention, initial administrations of hCG immunogenic peptide conjugates for treatment of cancer generally contained at least 1.0 mg of the hCG immunogenic peptide derivatized to a suitable carrier protein. The study results presented in Example 1 suggest that such doses do not result in an immune response to both the C-terminal epitope (CTP16, SEQ ID NO:6) and the N-terminal epitope (CTP21, SEQ ID NO:4) of hCG-CTP37 in the majority of patients under treatment and hence may not be an effective treatment regimen for colorectal cancer.

As further shown in Example 1, patients in a Phase II clinical trial who demonstrated an immune response to both the C-terminal epitope (CTP16, SEQ ID NO:6) and the N-terminal epitope (CTP21, SEQ ID NO:4) of hCG-CTP37 had significantly increased survival times.

The present invention is directed to methods for treatment of cancer that result in an immune response to both the C-terminal epitope (CTP16, SEQ ID NO:6) and the N-terminal epitope (CTP21, SEQ ID NO:4) of CTP37. This may be accomplished by administration of one or more of (1) less than 1.0 mg of hCG-CTP37 (SEQ ID NO:2) peptide/patient/administration, alone or in combination with an amount of "loop" peptide (SEQ ID NO:9), each derivatized to a suitable carrier molecule; (2) an hCG loop peptide (SEQ ID NO:9) derivatized to a suitable carrier, followed by administration of less than 1.0 mg of hCG-CTP37 (SEQ ID NO:2) peptide/patient/administration; (3) an hCG-CTP21 (SEQ ID NO:4) peptide vaccine, derivatized to a suitable carrier protein; (4) a human monoclonal antibody specifically immunoreactive with hCG-CTP21 (SEQ ID NO:4), administered at least once every 1 to 2 weeks; (5) a human monoclonal antibody specifically immunoreactive with hCG-CTP21 (SEQ ID NO:4) together with a human monoclonal antibody specifically immunoreactive with hCG- CTP16 (SEQ ID NO:6), administered at least once every 1 to 2 weeks; and (5) an hCG-CTP37 vaccine (SEQ ID NO:2) in combination with a human monoclonal antibody specifically immunoreactive with hCG-CTP21 (SEQ ID NO:4).

In one preferred embodiment, 0.5 mg of CTP37 (SEQ ID NO:2), derivatized to a suitable carrier molecule, is administered alone, or in combination with an amount of the "loop" peptide (SEQ ID NO:9). Typically, the amount of the "loop" peptide (SEQ ID NO:9) administered to a given patient is equal to, or greater than the amount of CTP37 (SEQ ID NO:2). For example, when the CTP37 vaccine is administered together with the "loop" vaccine, the amount of the CTP37 component of the vaccine is generally less than 1.0 mg, preferably 0.5 mg, and the amount of "loop" vaccine is patient is equal to, or greater than the amount of CTP37 (SEQ ID NO:2). In a further aspect of this embodiment from 25 to 500 mg of an anti-hCG CTP21 and/or anti-hCG CTP16 human monoclonal antibody is also administered to the patient, preferably about 1 to 2 times per week.

The amount of CTP37 (SEQ ID NO:2) plus or minus "loop" peptide (SEQ ID NO:9), in the treatment regimen and/or the amount of anti-hCG CTP21 and/or anti-hCG CTP16 human monoclonal antibody may be modified prior to successive administrations, based on the results of an immunoassay for anti-CTP37, anti-CTP16 and anti-CTP21 antibodies in a body fluid of the patient under treatment.

Preferred treatment regimens result in a detectable immune response to CTP37, CTP16 and CTP21, which has been correlated with increased survival time in colorectal cancer patients, as further detailed in Example 1.

VI. Evaluation of the Immune Response to hCG

Clinical endpoints useful in a determination of the efficacy of hCG vaccine administration include an evaluation of the immune response to: hCG-CTP37 (SEQ ID NO:2), hCG-CTP16 (SEQ ID NO:6), hCG-CTP21 (SEQ ID NO:4), a determination of tumor size and patient survival time (e.g., in weeks).

In one aspect, the invention provides a means for classifying the immune response to hCG in a cancer patient, e.g., 9 to 15 weeks after administration of an hCG vaccine; by measuring the level of antibodies against the C-terminal fragment of CTP37, hCG-CTP16 (SEQ ID NO:6), the N-terminal fragment of CTP37, hCG-CTP21 (SEQ ID NO:4), and CTP37, followed by classifying the patient into one of the following four groups, based on their immune response to hCG-CTP16, hCG-CTP21 and hCG-CTP37: (1) patients with no detectable anti-CTP37 antibody in their plasma (non-antibody responders); (2) patients in which total anti-hCG-CTP37 antibodies are detectable while neither anti-CTP16 or anti-CTP21 antibodies are detectable (poor antibody responders); (3) patients with detectable anti-CTP37 antibody and anti-CTP16 antibody, but no detectable anti-CTP21 antibody in their plasma (CTP16 only antibody responders); and (4) patients with detectable anti-CTP37, anti-CTP16 and anti-CTP21 antibody in their plasma (CTP16 and CTP21 antibody responders).

The present invention includes a diagnostic device for monitoring the immune response to hCG. The device includes a peptide having the amino acid sequence of the C-terminal fragment of hCG-CTP37 (hCG-CTP16, SEQ ID NO:6), a peptide having the amino acid sequence of the N-terminal fragment of hCG-CTP37 (hCG-CTP21, SEQ ID NO:4) and a reagent effective to label human antibodies, such as a reporter-labeled anti-human immunoglobulin antibody; in order to detect human antibodies that are immunoreactive with the peptides.

Such diagnostic devices are generally known to those of skill in the art of immunology and are routinely used to analyze antibodies in the body fluids of various subjects.

In some cases, the device includes a solid-phase substrate to which the hCG peptides are attached.

The invention further includes a method of monitoring the immune response to hCG by carrying out the steps of reacting a body-fluid sample with a peptide having the amino acid sequence of (1) the C-terminal fragment of hCG-CTP37 (hCG-CTP16, SEQ ID NO:6), (2) the N-terminal fragment of hCG-CTP37 (hCG-CTP21, SEQ ID NO:4), and (3) hCG-CTP37 (SEQ ID NO:2); and detecting antibodies in the sample that are immunoreactive with each peptide. It is preferred that the assay be quantitative and accordingly be used to compare the level of each antibody in order to determine the relative magnitude of the immune response to each peptide.

The methods of the invention are generally applicable to immunoassays, such as enzyme linked immunosorbent assay (ELISAs), radioimmunoassay (RIA), immunoprecipitation, Western blot, dot blotting, FACS analyses and other methods known in the art.

In one preferred embodiment, the immunoassay includes an hCG peptide antigen immobilized on a solid support, e.g., an ELISA assay.

It will be appreciated that the immunoassay may be readily adapted to a kit format exemplified by a kit which comprises: (A) one or more peptides having the amino acid sequence of (1) the C-terminal fragment of hCG-CTP37 (hCG-CTP16, SEQ ID NO:6); (2) the N-terminal fragment of hCG-CTP37 (hCG-CTP21, SEQ ID NO:4); and (3) hCG-CTP37 (SEQ ID NO:2) bound to a solid support; (B) a means for collecting a sample from a subject; and (C) a reaction vessel in which the assay is carried out. The kit may also comprise labeling means, indicator reaction enzymes and substrates, and any solutions, buffers or other ingredients necessary for the immunoassay.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following examples illustrates but are not intended in any way to limit the invention.

EXAMPLE 1

In a randomized Phase II clinical trial, 77 patients were assigned to either low or high dose vaccine regimens. Eligible patients had undergone curative resection of the primary tumor, were of any race, either sex, greater than 18 years of age and had a histologic diagnosis of adenocarcinoma of the colon or rectum that was metastatic. The trial design excluded concomitant chemotherapy. The protocol required a positive test for delayed-type hypersensitivity to one or more common recall antigens (tetanus toxoid, diphtheria toxoid, Streptokinase, tuberculin, Candida, trichophyton) as measured by intradermal skin tests. All patients tested negative for immediate-type hypersensitivity to diphtheria toxoid recall antigen by an intradermal skin test prior to vaccination. All patients had SWOG (Southwest Oncology Group) performance scores of 0, 1 or 2.

The vaccine was prepared as a hand-made emulsion of squalene:mannide oleate vehicle in a ratio of 4:1 (v:v) formulated with a CTP37-diphtheria toxoid conjugate (25 molecules synthetic CTP37 peptide/$10^5$ Da of DT) to nor-muramyl dipeptide adjuvant ratio of 20:1 (w:w) dissolved in sterile saline. The inoculation volume was 0.4 ml for 0.5 mg dose, 0.8 ml for 1.0 mg dose and 1.6 ml for a 2.0 mg dose (based upon conjugate weight). Thirty-six patients were enrolled into the low dose regimen which consisted of 0.5 mg vaccine on day 0, day 28, day 70 and week 16. Forty-one patients in the high dose regimen received 2.0 mg of vaccine on day 0 followed by 1.0 mg on day 28, day 70 and week 16. The vaccine was administered intramuscularly.

hCG-CTP37 (SEQ ID NO:2, FIG. 2A), is known to contain at least two epitopes, an N-terminal region (CTP21, SEQ ID NO:4, FIG. 2C), containing an epitope (SEQ ID NO:5, FIG. 2D) and a C-terminal region (CTP16, SEQ ID NO:6, FIG. 2E), containing an epitope (SEQ ID NO:8, FIG. 2G).

Clinical endpoints that were evaluated included the immune response to the N-terminal fragment of hCG-CTP37, hCG-CTP21 (SEQ ID NO:4); the C-terminal fragment of hCG-CTP37, hCH-CTP16 (SEQ ID NO:6); and the full CTP37 peptide (SEQ ID NO:2), a determination of tumor size and patient survival time.

The level of anti-hCG antibodies was measured by determining the binding of $^{125}$I-labeled hCG to varying dilutions of sera collected at intervals after immunization, as described previously (Jones W et al, Lancet 1:1295–1298, 1998). Results are reported as the amount of β-hCG bound in nmole per liter of undiluted serum.

A standard solid phase, indirect enzyme-linked immunosorbent assay (ELISA) was used for analysis of patient antisera for anti-DT antibodies. Briefly, 96 well microtiter plates were coated with purified DT (Pasteur Merieux Connaught, Toronto, Ontario, Canada) at a concentration of 1 μg/ml in phosphate-buffered saline (PBS). Serial two-fold dilutions of patient antisera were added to the wells in PBS/1% bovine serum albumen (BSA) and 0.1% Tween-20 and incubated for 1 hour at room temperature. Wells were washed with PBS/0.1% Tween-20 followed by the addition of a goat anti-human IgA, IgG, IgM-horseradish peroxide conjugate (HRP conjugate, Kierkegaard and Perry Laboratories, Gaithersburg, Md.) for 45 minutes. Following well washing with PBS/0.1% Tween-20 (twice) and distilled water (twice), plates were developed by the addition of chromogen (ABTS, Kierkegaard and Perry Laboratories, Gaithersburg, Md.) for 15 minutes and subsequently analyzed for absorbance at 405 nm. The results for all patient samples are reported as optical density at a selected dilution to (1/32000) which occurred in a linear titration range.

hCG-CTP16 (SEQ ID NO:6) and hCG-CTP21 (SEQ ID NO:4) were synthesized and purified by high performance liquid chromatography to >95% purity (Peptide Express, Colorado State University, Fort Collins, Colo., USA). hCG-CTP37 was obtained by GMP production (Peninsula Laboratories, Inc. Belmont, Calif., USA). Patient antisera with sufficient anti-hCG antibody titer was assayed for binding to CTP37, CTP21 and CTP16 using a competition ELISA. Prior to the competition ELISA, optimal antigen coating concentration and optimal antiserum dilution for the competition ELISA were determined for each antiserum by indirect ELISA. An ELISA plate coated with CTP37 at 1.0, 0.50, 0.25 and 0.10 μg/ml was blocked with 1% BSA in PBS. Several antiserum dilutions ranging from 1/1000 to 1/60,000 were added to the plate. Bound antibodies were detected with an anti-human HRP conjugate. The antigen coating concentrations that produced linear responses of optical densities to antiserum concentrations were used in the competition ELISA. The competition ELISA was performed according to the method described elsewhere with modifications (Chang SP et al., J Immunol 128: 702–705, 1982). Briefly, plates were incubated with CTP37 overnight in PBS at a pre-determined concentration for each antiserum and then blocked with 1% BSA/PBS. Next, the antiserum at the pre-determined dilution was preincubated with various concentrations of CTP37, CTP21 or CTP16 and then 60 μl of each of the antiserum-peptide mixtures was added to each well of the CTP37-coated plate. HRP-conjugated human immunoglobulin was used to determine the amount of free (not competed away) antibodies bound to the plate. Binding percentages were calculated by comparing the sample optical densities at 405 nm to the antiserum standard series (without competing peptides) on the same plate. Two replicate values for each peptide concentration were averaged and plotted as % binding vs. $\text{Log}_{10}$[peptide competitor], then fitted with the one site competition equation using GraphPad PRISM™ software (GraphPad Software, Inc. San Diego, Calif.). Microsoft Excel and GraphPad PRISM™ software were used for statistical analyses including Kaplan-Meier curves to display survival and log-rank tests to compare survival. P-values of 0.05 or less were considered significant.

The immune response to hCG was measured in the serum of patients from 0 to 24 weeks post initiation of vaccination. Significant hCG antibody production was observed by week 12 of the vaccination protocol (FIG. 3).

Figure 4:
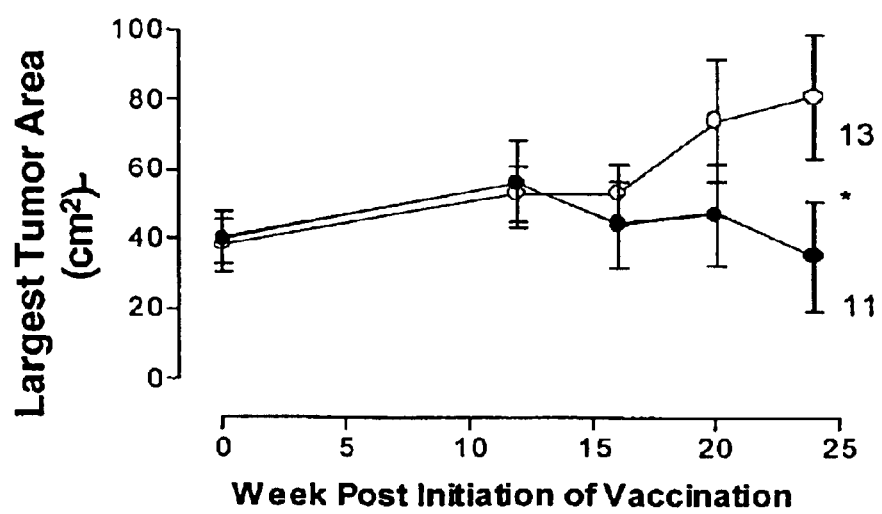
FIG. 4 depicts the largest tumor area (cm$^2$) over 0 to 24 weeks post initiation of vaccination with CTP37, for colorectal cancer patients in the low dose group (closed circles) and the high dose group (open circles), of a Phase II clinical trial, as described above for FIG. 3.
Figure 5:
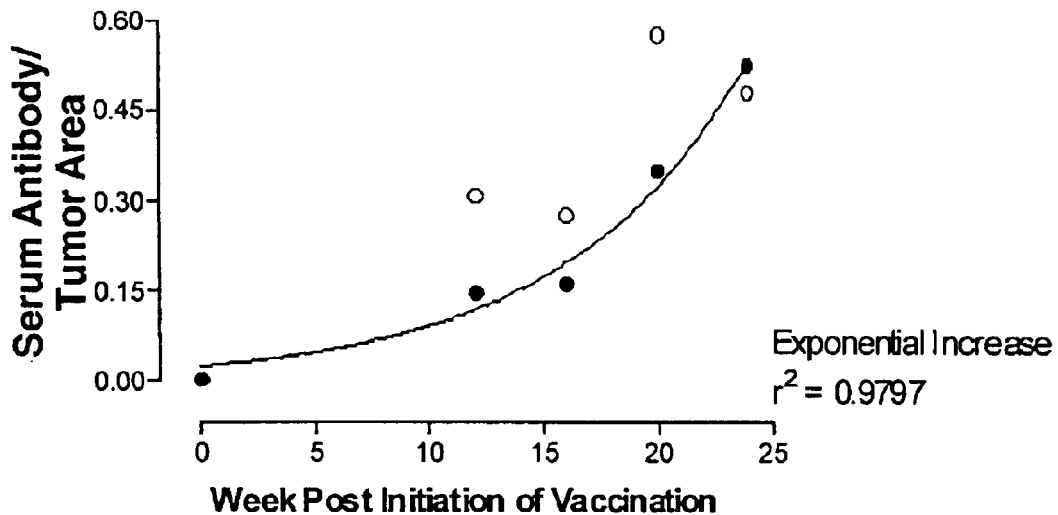
FIG. 5 depicts the relationship between the serum anti-CTP37 antibody level and tumor area (cm$^2$) for colorectal cancer patients in a Phase II clinical trial over 0 to 24 weeks post initiation of vaccination with CTP37, as described for FIG. 3.

The anti-hCG CTP37 antibody titer was dose dependent, as the 2.0 mg initial dose of vaccine resulted in greater antibody titer than the 0.5 mg dosing regimen (FIG. 3). Although the largest tumor area did not significantly increase in patients receiving the low dose, tumor growth was observed in the high dose regimen and the average largest tumor area was significantly different between the two dose regimens (p<0.05, FIG. 4). Hence the immune response to CTP-37 did not correlate with the average largest tumor area. In addition, patient median survival time was 39.9 weeks for the low dose group and 32.4 weeks for the high dose group. The antibody/largest tumor area ratio increased exponentially with time (FIG. 5).

Figure 6:
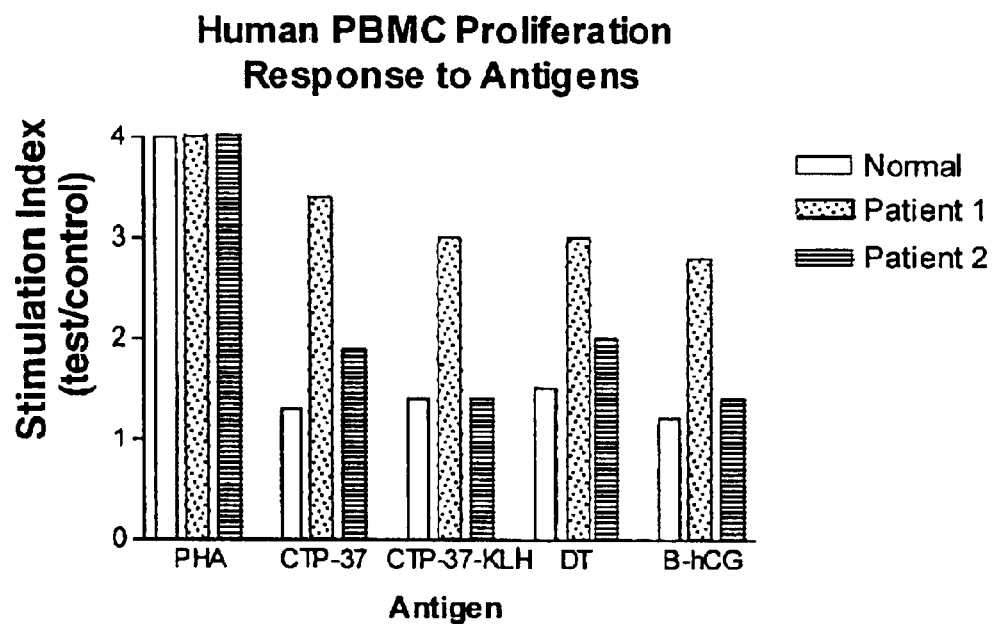
FIG. 6 presents the cell-mediated immune response of two colorectal cancer patients immunized with CTP37 (in an extended protocol of the Phase II clinical trial, described above for FIG. 3), relative to that of a normal unimmunized subject. The PBMC proliferation response to various antigens (PHA, CTP-37, CTP-37-KI, DT and β-hCG) is shown.

The vaccine was also shown to generate a cell-mediated immune response as determined by the PBMC proliferation response to various antigens (PHA, CTP-37, CTP-37-KI, DT and μ-hCG). The mitogen was added at 1, 0.1, or 0.01 μg/well (data presented in FIG. 6 are from the 1 μg/ml concentration). The PHA stimulation index was greater than 4, hence, FIG. 6 is not correct for those data points. The correct values for PHA are 79 for normal; 147 for patient 1; and 2819 for patient 2. The method is further described in Triozzi, et al., 1997.

The antibody response to CTP-37 was correlated with patient survival, however, the DT antibody titer was not correlated with patient survival for either the high or low dose groups.

Although the mechanism underlying the discovery is not part of the claimed invention, the results suggest that the antibody response to particular hCG beta subunit epitopes may act via pharmacokinetic (enhanced clearance of hCG) and/or pharmacodynamic (interference with hCG binding to receptors) mechanisms. Evaluation of serum samples taken from patients immunized with CTP37 in a competition assay with either the CTP16 or CTP21 peptides of CTP37, indicated a greater immune response to CTP16 relative to the immune response to CTP21, suggesting that CTP16 is immunodominant in humans.

The immune response of patients who received an intramuscular injection of CTP37-DT fell into 4 groups as follows: (1) patients in which neither first nor second antibodies, nor total anti-hCG-CTP37 antibodies are detectable (non-antibody responders); (2) patients in which in which total anti-hCG-CTP37 antibodies are detectable while neither first nor second antibodies are detectable (poor antibody responders); (3) patients having a detectable level of first antibodies, but undetectable levels of second antibodies (CTP16 only antibody responders); and (4) patients having detectable levels of both first and second antibodies (CTP16 and CTP21 antibody responders) (Table 1).

response. The median survival time of dual-epitope responders was 65 weeks, which represents a longer survival duration compared to patients treated with irinotecan. The overall mean anti-hCG titer in the patients who were capable of developing antibodies against both CTP37 epitopes was not significantly different compared to those patients only capable of developing a response against the CTP16 epitope (Table 1). The median survival time, however, was nearly twice as long in the dual-epitope responder group compared to the single epitope group. These results indicate that the qualitative nature of the immune response against β-hCG may play a role in determining vaccine efficacy and, in addition, the results support the hypothesis that the antibody response against β-hCG is directly associated with patient survival.

TABLE 1

Patient Characteristics of Four Antibody Response Subpopulations.

| Group | Patients | Detected anti-CTP37 antibody | Detected anti-CTP16 antibody | Detected anti-CTP21 antibody | Serum hCG | hCG antibody (nM) |
|---|---|---|---|---|---|---|
| 1 | 21 | NO | NO | NO | 3.5 ± 2.9 | 0 ± 0 |
| 2 | 20 | YES | NO | NO | 5.3 ± 3.4 | 2.4 ± 1.4 |
| 3 | 20 | YES | YES | NO | 7.5 ± 15.7 | 36.6 ± 51.5 |
| 4 | 15 | YES | YES | YES | 3.6 ± 3.5 | 30.0 ± 23.6 |

Figure 7:
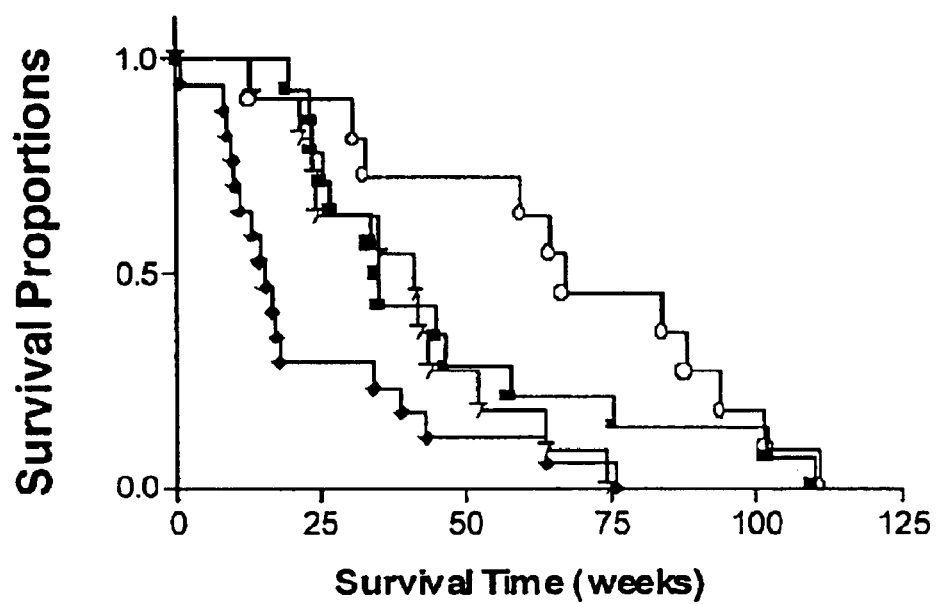
FIG. 7 presents the proportion of surviving patients versus survival time for colorectal cancer patients immunized with CTP37 (in an extended protocol of the Phase II clinical trial, described above for FIG. 3), and characterized as follows: (1) patients with no detectable anti-CTP37 antibody in their plasma (closed diamonds); (2) patients with a low level of detectable anti-CTP37 antibody in their plasma, such that the relative level of antibody to CTP16 versus CTP21 could not be determined (open triangle); (3) patients with detectable anti-CTP37 antibodies and anti-CTP16 antibodies, but no detectable anti-CTP21 antibodies in their plasma (closed squares); and (4) patients having detectable anti-CTP37, anti-CTP16 and anti-CTP21 antibodies in their plasma (open circles).

The survival curves for patients in each of the four antibody response groups is shown in FIG. 7. These survival curves were found to be significantly different from each other ($p=0.0019$). Median survival times were 16.4 weeks for the 21 patients with no anti-hCG antibodies, 29.6 weeks in the 20 patients comprising the poor antibody titer response group, 34.8 weeks in the 20 patients with only CTP16 epitope recognition, and 64.6 weeks in the 15 patients mounting a response to both CTP16 and CTP21, as summarized in Table 2, below.

TABLE 2

Immune response to CTP37 in Phase II Clinical Trial

| Group | Patients in group | Survival time (weeks) |
|---|---|---|
| 1 | 21/73 | 16.4 |
| 2 | 20/73 | 29.6 |
| 3 | 20/73 | 34.8 |
| 4 | 15/73 | 64.6 |

In addition, the increased survival time for patients with a detected immune response to both CTP16 and CTP21 was predictive of increased survival time for both high and low dose treatment groups.

The survival benefit for patients with antibody recognition of both the CTP16 and the CTP21 epitopes in the CTP37 vaccine ("dual epitope response") was not related to a general measure of patient overall immune status. As shown in Table 1, there were no significant differences between the four groups in average serum IgG levels. In addition, there was no difference in the number of recall antigens responded to, or the magnitude of recall antigen response in a skin test prior to administration of the CTP37 peptide vaccine. Furthermore, no significant difference in mean anti-hCG antibody titer was observed in comparing the CTP16 only, and CTP16 and CTP21 responder groups.

The results presented herein demonstrate that survival time increased as patients developed a dual-epitope

EXAMPLE 2

Rabbits were immunized with CTP37 and the immune response to CTP16 and CTP21 was measured. A greater immune response to CTP16 was detected relative to the immune response to CTP21 in a competition immunoassay, indicating that, similar to humans, CTP16 is immunodominant in rabbits (Table 3).

When rabbits were immunized with the hCG "loop" peptide alone, an immune response to CTP16 was detected in competition assay, while no response to CTP21 was detected, and when rabbits were immunized with CTP37 and the loop peptide, an immune response to both CTP16 and CTP21 was detected in the competition assay. Following the combined administration of CTP37 and hCG "loop" peptide vaccines, the immune response to CTP16 did not appear to be immunodominant.

TABLE 3

Epitope Mapping and Bioneutralization[1]

| Antisera Against | Rabbit # | Peptide Competitor | | Bioneutralization | |
|---|---|---|---|---|---|
| | | CTP21 | CTP16 | MUT | Receptor |
| CTP37 | 4162 | + | ++ | +++ | − |
| | 4164 | ++ | + | ++ | + |
| | 77 M | − | + | − | − |
| | 63 H | − | ++ | − | N.D.[3] |
| | 3989 | − | +++ | Pro Effect[2] | N.D. |
| LOOP | 4157 | − | ++ | +++ | ++ |
| | 4160 | − | +++ | +++ | ++ |
| COMBINED LOOP + CTP37 | 4165 | ++ | + | + | N.D. |
| | 4166 | ++ | + | +++ | N D. |
| | 4169 | + | ++ | ++ | N.D. |
| | 4173 | ++ | + | ++ | N.D. |

[1] + = ED 50 > 1000 ng; ++ = ED 50 < 250 ng; +++ = ED 50 < 10 ng
[2] Pro Effect = greater hCG response than the no antiserum control
[3] N.D. = not done The results from these immunization studies on the combined administration of the CTP37 peptide vaccine and the hCG "loop" vaccine indicate that co-administration of the CTP37 and "loop" peptides results in an enhanced immune response to CTP21 and a similar magnitude of immune response to both CTP16 and CTP21, suggesting that the "loop" peptide may be effective as a booster vaccine, resulting in a more balanced immune response to hCG-CTP16 and hCG CTP21, than administration of CTP37 alone.

TABLE 4

Table Of Sequences

| Description | SEQ ID NO | FIG. |
|---|---|---|
| hCG beta subunit from GenBank- Accession number 180437 | 1 | 1 |
| hCG-CTP37 peptide: TCDDPRFQDSSSSKAPPPSLPSPSRLPGPSDTPILPQ (residues 129–165 of beta subunit of hCG) | 2 | 2A |
| hCG-CTP38 peptide: MTCDDPRFQDSSSSKAPPPSLPSPSRLPGPSDTPILPQ (residues 129–165 of beta subunit of hCG + N-terminal met) | 3 | 2B |
| N-terminal epitope, CTP21: CDDPRFQDSSSSKAPPPSLPS (residues 130–150 of the CTP of the beta subunit of hCG) | 4 | 2C |
| epitope within CTP21: DDPRFQDS (8mer peptide corresponding to residues 131–138 of beta subunit of hCG) | 5 | 2D |
| C-terminal epitope, CTP16: SPSRLPGPSDTPILPQ (residues 150–165 of the CTP of the beta subunit of hCG) | 6 | 2E |
| C-terminal epitope with added N-terminal C, CTP-17: CSPSRLPGPSDTPILP | 7 | 2F |
| epitope within CTP16/CTP17: RLPGPSDTPILP (corresponding to residues 153–165 of beta subunit of hCG) | 8 | 2G |
| hCG beta subunit loop peptide CTP MTR VLQ GVL PAL PQV VC (residues 58–77 of beta subunit with an S-S bond between residues 58 and 77) | 9 | 2H |

It is claimed:

1. A method of treating a cancer that secretes hCG in a subject comprising:

administering to the subject, a therapeutically effective dose of a human or humanized monoclonal antibody specifically immunoreactive with a peptide consisting of a 21 mer N-terminal fragment of hCG-CTP37 (hCG-CTP21, SEQ ID NO:4); and administering to the subject, a vaccine composed of a peptide consisting of hCG-CTP37 (SEQ ID NO:2), conjugated to a suitable carrier protein.

* * * * *